(12) United States Patent
Smith et al.

(10) Patent No.: US 8,039,669 B2
(45) Date of Patent: Oct. 18, 2011

(54) CATALYTIC METATHESIS OF SECONDARY AMIDES

(75) Inventors: Christen Bell Smith, Madison, WI (US);
Denis A. Kissounko, Madison, WI (US);
Samuel H. Gellman, Madison, WI (US);
Shannon S. Stahl, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 504 days.

(21) Appl. No.: 12/325,484

(22) Filed: Dec. 1, 2008

(65) Prior Publication Data
US 2009/0299098 A1 Dec. 3, 2009

Related U.S. Application Data

(60) Provisional application No. 61/013,190, filed on Dec. 12, 2007.

(51) Int. Cl.
*C07C 231/08* (2006.01)
(52) U.S. Cl. ........ 564/185; 564/170; 564/179; 564/182; 564/218; 564/219
(58) Field of Classification Search ................. None
See application file for complete search history.

(56) References Cited

U.S. PATENT DOCUMENTS 7,154,004 B2  12/2006  Stahl et al.

OTHER PUBLICATIONS

Bell et al., Angewandte Chemie, International Edition (2007), 46(5), p. 761-763.*
Chesney, A.; Steel, P. G.; Stonehouse, D. F., High Loading Cellulose Based Poly(alkenyl) Resins for Resin Capture Applications in Halogenation Reactions, *J. Comb. Chem.* 2000, 2, 434-437.
Estep, K. G.; Neipp, C. E.; Stephens Stramiello, L. M.; Adam, M. D.; Allen, M. P.; Robinson, S.; Roskamp, E., Indole Resin: A Versatile New Support for the Solid-Phase Synthesis of Organic Molecules, J. *J Org. Chem.* 1998, 63, 5300-5301.
Furuya, Y.; Ishihara, K.; Yamamoto, H., Cyanuric Chloride as a Mild and Active Beckmann Rearrangement Catalyst, *J Am. Chem. Soc.* 2005,127,11240-11241.
Katritzky, A. R.; Cai, C.; Singh, S. K., Efficient Microwave Access to Polysubstituted Amidines from Imidoylbenzotriazoles, *J. Org. Chem.* 2006, 71, 3375-3380.
Lee, S. I.; Son, S. U.; Chung, Y. K., Catalytic one-pot synthesis of N-phenyl alkyl amides from alkene and aniline in the presence of cobalt on charcoal under carbon monoxide, *Chem. Commun.* 2002, 12, 1310-1311.
Mariella, R. P.; Brown, K. H., Diacetylation of amines, *J. Org. Chem.* 1971, 36, 735-737.
Minisci, F.; Punta, C.; Recupero, F.; Fontana, F.; Pedulli, G. F., Aerobic Oxidation of N-Alkylamides Catalyzed by N-Hydroxyphthalimide under Mild Conditions. Polar and Enthalpic Effects, *J Org. Chem,* 2002, 67,2671-2676.
Shine, S. J.; Yueh, W., Reactions of Thianthrene Cation Radical with Acyclic and Cyclic Alcohols, *J. Org. Chem,* 1994, 59, 3553-3559.
Tsuji, Y.; Yoshii, S.; Ohsumi, T.; Kondo, T.; Watanabe, Y., Dodecacarbonyltriruthenium catalyzed one-to-one addition of iv-substituted formamides to olefins, *J Organometallic Chem.* 1987, 331, 379-385.
Wan, Y.; Alterman, M.; Larhed, M.; Hallberg, A., Dimethylformamide as a Carbon Monoxide Source in Fast Palladium-Catalyzed Aminocarbonylations of Aryl Bromides, *J. Org. Chem.* 2002, 67,6232-6235.
Zeng, Q.-H.; Hu, X.P.; Duan, Z.-C.; Liang, X.-M.; Zheng, Z., Unsymmetrical Ferrocenylethylamine-Derived Monophosphoramidites: Highly Efficient Chiral Ligands for Rh-Catalyzed Enantioselective Hydrogenation of Enamides and Ɒ-Dehydroamino Acid Derivatives, *J. Org. Chem*, 2006, 71, 393-396.

* cited by examiner

*Primary Examiner* — Brian J Davis
(74) *Attorney, Agent, or Firm* — Joseph T. Leone, Esq.; DeWitt Ross & Stevens S.C.

(57) ABSTRACT

The invention provides methods and reagents for the metathesis of secondary amides via a transacylation mechanism employing catalytic quantities of an imide initiator and a Brønsted base. Equilibrium-controlled exchange between various amide reactant pairs is demonstrated for substrates bearing a variety of N-alkyl and N-aryl substituents.

13 Claims, 2 Drawing Sheets

CATALYTIC METATHESIS OF SECONDARY AMIDES

CROSS-REFERENCE TO RELATED APPLICATIONS

This application claims the benefit of U.S. provisional application No. 61/013,190, filed Dec. 12, 2007, which is incorporated herein by reference in its entirety.

STATEMENT REGARDING FEDERALLY SPONSORED RESEARCH

This invention was made with United States government support awarded by the following agencies: NSF Grant No. 0404704. The United States government has certain rights in this invention.

FIELD OF THE INVENTION

The present invention is directed to the field of dynamic covalent chemistry. More specifically, the present invention provides a method and reagents for equilibrium-controlled catalytic metathesis of secondary amides.

BACKGROUND OF THE INVENTION

Reactions that interconvert strong covalent bonds, termed "dynamic covalent chemistry" (DCC), offer a powerful approach for thermodynamically controlled synthesis of organic molecules with interesting structures and/or properties. DCC involving esters, thioesters, imines and disulfides, among other functional groups, has provided access to useful new molecules and molecular insights. Such efforts to date have focused on bonds that were previously known to be readily exchangeable. Extension of the DCC approach to other types of functional groups will require advances in organic reactivity and catalysis. It would be valuable, for example, to implement DCC with carboxamide-containing molecules, but the low intrinsic reactivity of the carboxamide group has hampered efforts to achieve this goal. Identifying catalysts that induce amide metathesis, i.e., the interconversion of carboxamides based on cleavage and formation of the N-acyl bonds [(Eq. 1)], represents a fundamental challenge in organic reactivity. The inventors recently described metal-catalyzed transamidation reactions [(Eq. 2)], which, in principle, offer a pathway to amide metathesis. Subsequent studies, however, revealed that secondary amide metathesis is not successful under the original transamidation conditions.

One of the few previous examples of amide metathesis involves the use of proteases under conditions compatible with both peptide hydrolysis and synthesis. Limitation associated with these reactions include limited substrate scope and long reaction times.

As can be appreciated, there is a long felt need in the chemical arts for methods and reagents, such as small-molecule catalysts, that facilitate secondary amide metathesis. Such desirable technologies would certainly broaden the practical applications of dynamic covalent chemistry.

SUMMARY OF THE INVENTION

Here, the inventors demonstrate an alternative and mechanistically novel strategy for catalytic amide metathesis involving imide-mediated transacylation. Their results provide the necessary foundation and guidance to implement amide-based DCC.

Accordingly, the present invention provides a method for the catalytic metathesis of secondary amides. Such a method includes the step of reacting in an aprotic solvent two or more distinct secondary amides in the presence of a Brønsted base and an imide initiator or precursor thereof. A catalytic metathesis reaction takes place in which acyl group exchange occurs between the two or more distinct secondary amides.

Methods according to the invention utilize a Brønsted base such as, for example, a Grignard reagent, alkyl- or aryl-lithium reagent, salt of conjugate base of amine and salt of conjugate base of alcohol. In certain embodiments, the Brønsted base is selected from the group consisting of NaN(SiMe$_3$)$_2$, KN(SiMe$_3$), KH, MeMgCl, KOtBu and LiN(SiMe$_3$)$_2$.

Imide initiators useful in the invention include, but are not limited to, acyclic imides such as N-benzyldiacetamide or N-methyldiacetamide. In certain embodiments, the imide initiator is provided in precursor form which provides, in situ, the respective imide initiator. Suitable precursors include acylating agents such as, for example, acyl halide, acyl imidazole, carboxylic acid anhydride, carboxylic acid ester and mixed anhydride molecules. Particularly preferred precursors include acetyl chloride and acetyl imidazole.

The inventive methods are generally carried out at a reaction temperature of about 90° C. to about 120° C. in an aprotic solvent, more preferably a polar, aprotic solvent.

Methods according to the invention display robustness for a wide range of secondary amide substrates. For example, two distinct secondary amides subjected to metathesis in the method may be an N-aryl/N-aryl amide reactant pair, an N-aryl/N-alkyl amide reactant pair, or an N-alkyl/N-alkyl amide reactant pair. In certain embodiments directed to N-alkyl/N-alkyl amide reactant pairs, those pairs are preferably provided in non-enolizable forms.

As can be appreciated, it is one object of the present invention to provide an approach for catalytic metathesis of secondary amides which provides a novel equilibrium-controlled mechanism. This invention provides the advantage over prior technologies in that it represents a powerful approach for thermodynamically controlled synthesis of industrially-useful molecules, including improved access to controlled reaction rates and resulting molecules with novel biological activity and therapeutic applications. Other objects, features and advantages of the present invention will become apparent after review of the specification, claims and drawings.

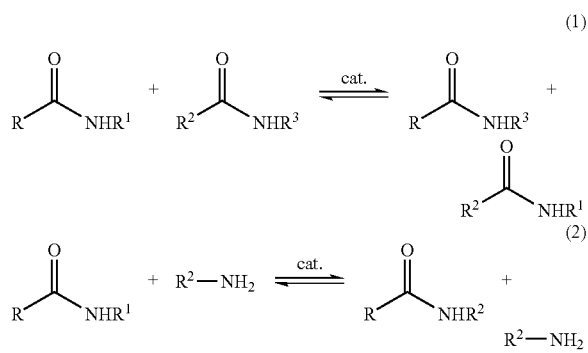

(0.23 mmol; 1 and 2 for the forward reaction, or 3 and 4 for the reverse reaction), base (0.046 mmol); 5 (0.046 mmol), diglyme (0.8 mL), 120° C., 18 h. Amide ratio was determined by GC analysis ($Ph_3CH$ internal standard). Each bar represents the average of five runs.

Figures 2A, 2B:
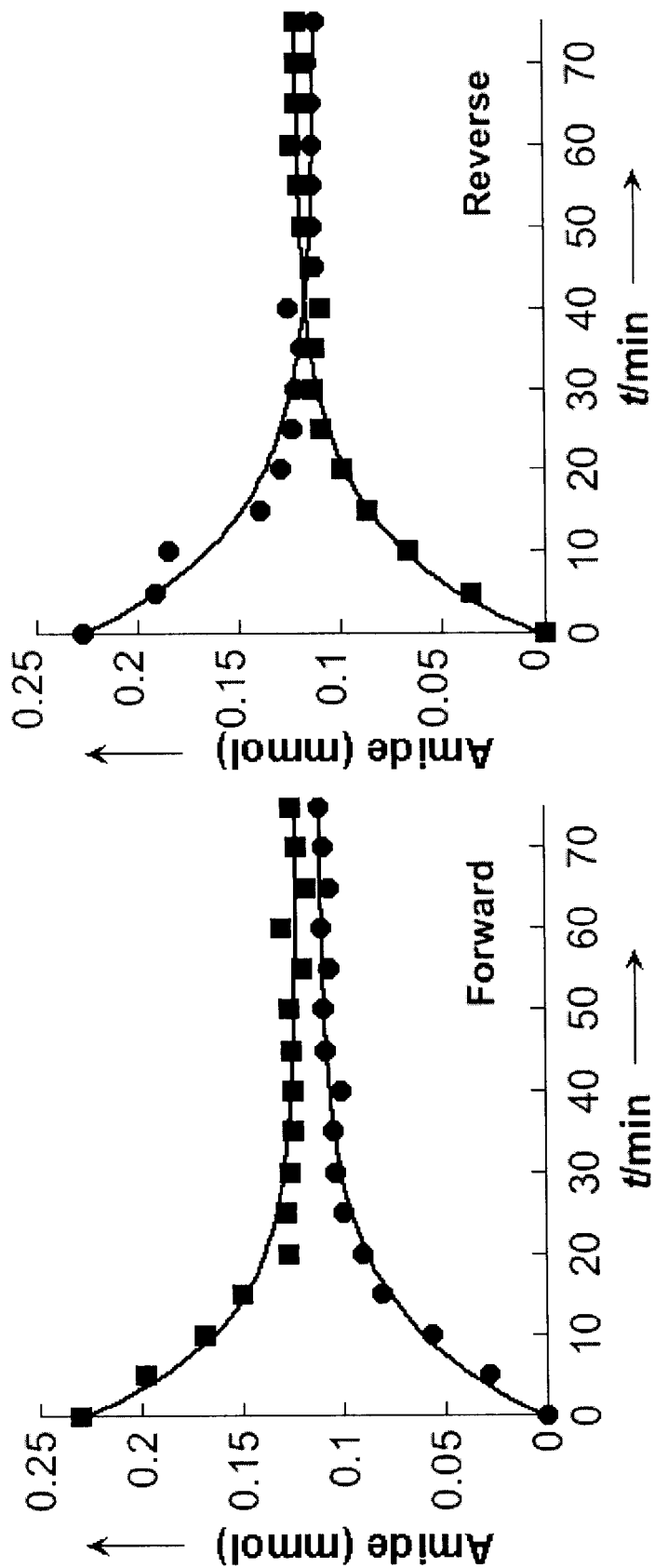

FIG. 2 depicts plots of the approach to equilibrium for Equation (5) both in forward and reverse directions (based of GC analysis of carboxamides 7 and 9). Squares: 7, circles: 9. Reaction conditions: 7 and 9 (0.23 mmol), KH (0.092 mmol), 11 (0.046 mmol), diglyme (0.8 mL), 90° C.

DETAILED DESCRIPTION OF THE INVENTION

When used in the context of the presently described methodology and reagents, the term "secondary amide" shall mean a carboxamide-containing molecule having the functional group —(CO)NHR, the nitrogen atom substituted by R which is not a hydrogen atom. Accordingly, the reactions described and claimed herein are secondary amide metathesis reactions between two or more carboxamide-containing molecules that result in the interconversion of the respective carboxamides based on cleavage and formation of N-acyl bonds.

In developing the present methods for equilibrium-controlled catalytic metathesis of secondary amides, the inventors discovered that sub-stoichiometric quantities of an acyclic imide and a Brønsted base, the latter to generate amidate species, would promote acyl group exchange between secondary amides [Eq. (3)]. Successive reactions of this type then enable equilibrium-controlled metathesis of secondary amides.

Figure 1:
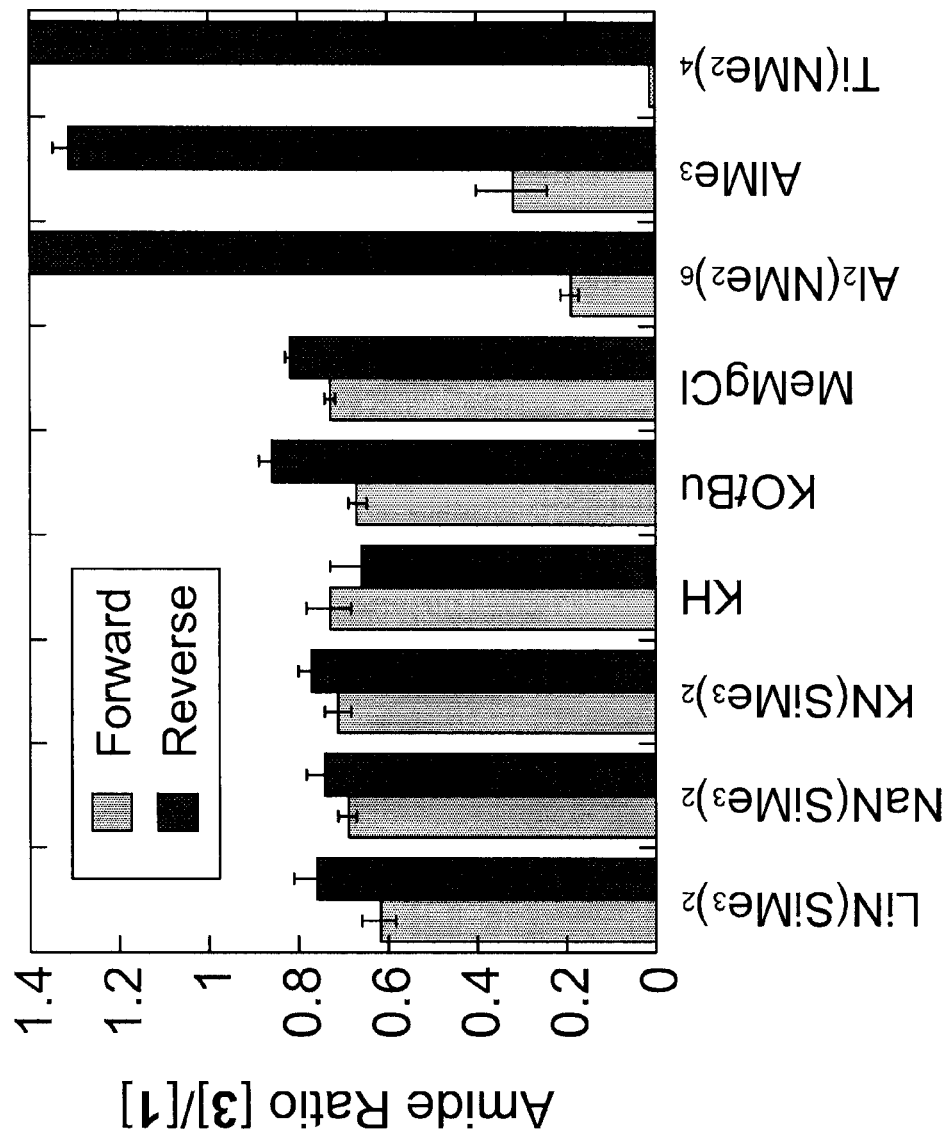
FIG. 1 illustrates results from the screening of bases for Equation (4). Reaction conditions: 1:1 mixture of amides

Initial efforts to promote the metathesis of N-benzylheptanamide and acetanilide [Eq. (4); Bn=benzyl] with di-N-acetylbenzlamine (5) as the imide established the feasibility of the inventive strategy. The effectiveness of several different bases was evaluated by comparing the amide ratio [3]/[1] obtained when the reaction was conducted in both the forward and reverse direction. Reactions that achieve equilibrium produce a [3]/[1] ratio that is independent of the reaction direction. FIG. 1 shows that the most effective bases are $NaN(SiMe_3)_2$, $KN(SiMe_3)_2$, and KH; in all three cases equilibrium is achieved. Significant amide exchange was observed also for MeMgCl, COtBu, and $LiN(SiMe_3)_2$. Metal complexes previously shown to promote transamidation, $[Al_2(NMe_2)_6]$ and $[Ti(NMe_2)_4]$, do not promote amide metathesis.

Several different pairs of secondary amides were evaluated under the metathesis conditions (Table 1). The inventors examined three classes of amide reactant pairs (N-aryl/N-aryl, N-aryl/N-alkyl and N-alkyl/N-alkyl). Each of the reactions was performed in both forward and reverse directions to determine whether equilibrium was achieved. Metathesis of N-aryl/N-aryl (Table 1; entries 1-3) and N-aryl/N-alkyl amide pairs (Table 1; entries 4-9) generally goes to completion, within the error limits of the product analysis. The presence of a bulky branched alkyl substituent on the amide nitrogen does not appear to hinder the exchange (Table 1; entry 7).

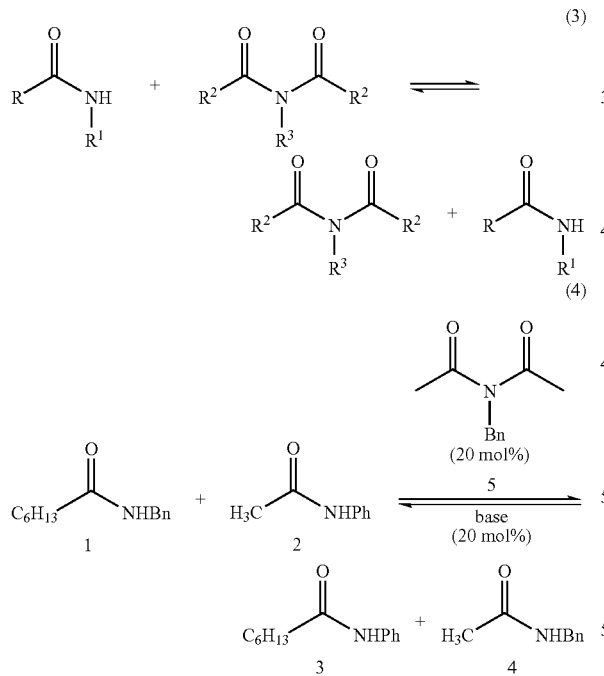

The preferred embodiment of carrying out catalytic metathesis of secondary amides according to the invention will now be described. The embodiment's description is offered for illustrative purposes only, and is not intended to limit the scope of the present invention. Indeed, various modifications of the invention in addition to those shown and described herein will become apparent to those skilled in the art from the present description and fall within the scope of the appended claims.

TABLE 1

| | Metathesis of Pairs of Secondary Amides[a] | | | |
| --- | --- | --- | --- | --- |
| | | | Amide Ratio B/A[b] | |
| Entry | R | $R^1$ | Forward | Reverse |
| | R = aryl | $R^1$ = aryl | | |
| 1 | Ph | p-MeOC$_6$H$_4$ | 0.91 (0.07) | 1.04 (0.08) |
| 2 | Ph | p-tolyl | 1.02 (0.03) | 1.09 (0.04) |
| 3 | p-tolyl | p-FOC$_6$H$_4$ | 0.77 (0.01) | 0.83 (0.03) |
| | R = alkyl | $R^1$ = aryl | | |
| 4 | Bn | Ph | 0.73 (0.05) | 0.66 (0.07) |
| 5 | Bn | p-MeOC$_6$H$_4$ | 0.64 (0.05) | 0.72 (0.07) |
| 6 | Bn | p-FOC$_6$H$_4$ | 0.66 (0.04) | 0.69 (0.02) |
| 7 | H,Me,C,Ph (chiral) | Ph | 0.69 (0.06) | 0.61 (0.06) |

TABLE 1-continued

Metathesis of Pairs of Secondary Amides[a]

| | R | R¹ | Forward | Reverse |
|---|---|---|---|---|
| 8 | 4-MeO-C₆H₄-CH₂- | Ph | 0.95 (0.06) | 0.88 (0.05) |
| 9 | 4-F-C₆H₄-CH₂- | Ph | 0.87 (0.07) | 0.81 (0.01) |
| 10 | R = alkyl, CHMePh (H, Me, Ph on C) | R¹ = alkyl, Bn | 0.98 (0.06) | 0.69 (0.02) |
| 11 | 4-MeO-C₆H₄-CH₂- | Bn | 0.73 (0.02) | 0.87 (0.02) |

[a]Reaction conditions: 1:1 mixture of amides (0.23 mmol each); KH (0.046 mmol); imide 5 (0.046 mmol), 0.8 mL of diglyme, 120° C., 18 h.
[b]Amide ratio determined by GC (internal standard = Ph₃CH). Data represent the average of five runs; standard deviation in parentheses.

Metathesis on N-alkyl/N-alkyl amide pairs proved to be more challenging. Partial exchange was observed, but these reactions did not achieve equilibrium in 18 h (Table 1; entries 10 and 11) under the standard conditions. No further exchange was observed at longer reaction times (36 h). Imide decomposition, perhaps involving α-deprotonation, could prematurely terminate the metathesis process and account for this observation. To test this hypothesis, the inventors examined the exchange between non-enolizable amide substrates (Table 2). Since the imide initiator incorporates the acyl fragments of the amide substrates during the reaction, the use of non-enolizable amide substrates should minimize imide α-deprotonation, even if 5 is initially the imide component.

TABLE 2

Metathesis of Pairs of Nonenolizable Amides[a]

R-C(=O)-NHR¹ (A) + Ph-C(=O)-NHR² ⇌ (forward/reverse) R-C(=O)-NHR² (B) + Ph-C(=O)-NHR¹

| Entry | R | R¹ | R² | Forward | Reverse |
|---|---|---|---|---|---|
| 1 | p-tolyl | Bn | CHMePh | 0.82 (0.02) | 0.83 (0.04) |
| 2 | C₆H₁₃ | Bn | CHMePh | 0.58 (0.11) | 0.92 (0.05) |

[a]See footnote [a] from Table 1 for reaction conditions and analytical methods.

This strategy proved to be successful: equilibrium was achieved with an N-alkyl/N-alkyl substrate pair (Table 2; entry 1). When only one of the starting amides was non-enoblizable, however, equilibrium was not achieved (Table 2; entry 2).

Imide initiator 5, employed in each of the reactions presented in Tables 1 and 2, is not commercially available. However, the commercially available imide N-methyl diacetamide (6) is equally effective as an amide metathesis initiator (Table 3, entry 1). Even more significant is the finding that simple acylating agents, acetyl chloride and acetylimidazole, promote amide metathesis (Table 3, entries 2 and 3). The latter reagents, which presumably form imides in situ, are attractive because they minimize the quantity of initiator-derived acyl and amine fragments present in the reaction.

TABLE 3

Alternative Initiators for Amide Metathesis [Eq. (4)][a]

| Entry | Initiator | Forward | Reverse |
|---|---|---|---|
| 1 | N-methyl diacetamide (6) | 0.83 (0.02) | 0.88 (0.03) |
| 2 | acetyl chloride | 0.73 (0.08) | 0.82 (0.05) |
| 3 | acetylimidazole | 0.73 (0.05) | 0.81 (0.05) |

[a]Reaction conditions: 1:1 mixture of amides (0.23 mmol each; 1 and 2 for the forward reaction, 3 and 4 for the reverse reaction), KH (0.046 mmol); initiator (0.046 mmol), diglyme (0.8 mL), 120° C., 18 h.
[b]Amide ratio determined by GC (internal standard = Ph₃CH). Data represent the average of five runs; standard deviation in parentheses.
[c] KH (0.092 mmol). The requirement for a two-fold excess of base relative to the acylating agent presumably reflects the formation of the imide in situ; that is one equivalent of base is consumed in the formation of the imide.

For example, N-methylamide side products are observed when 6 is used as the initiator, but no analogous side products are possible when either acetyl chloride or acetylimidazole is used. Furthermore, acid chlorides bearing an acyl fragment that matches one (or both) of the amide substrates can be readily obtained from the corresponding carboxylic acids. The inventors performed the reaction in Eq. (5), which features non-enolizable substrates together with N-benzoylimidazole as the initiator.

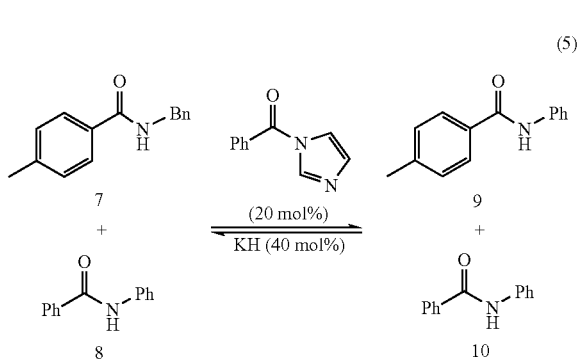

(5)

As the plots of the forward and reverse reactions against time reveal (FIG. 2), the reaction achieves equilibrium within approximately 1 h at 90° C. The exchange reaction in Equation (6), which features an N-butylamide, proceeds to equilibrium with acetyl chloride as the initiator. This result complements the data in Table 1 and Table 2, which feature N-benzylic substrates and an N-benzylimide inititator.

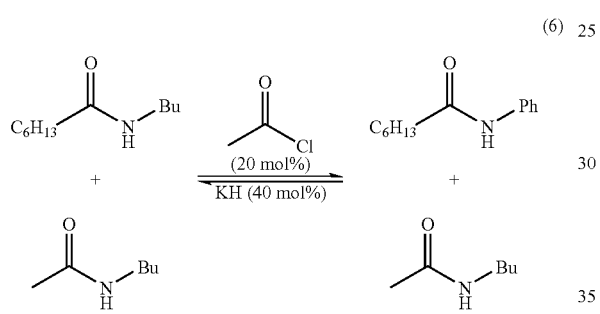

(6)

As can be appreciated, the inventors have demonstrated and describe herein that metathesis of secondary amides can be achieved through the combined action of simple acylating agents and Brønsted bases. These findings establish a novel strategy for inducing carboxamide exchange reactivity. Accordingly, the present disclosure provides a basis for implementing carboxamide-based dynamic covalent chemistry.

Accordingly, the present invention encompasses a method for the catalytic metathesis of secondary amides. Such a method includes the step of reacting in an aprotic solvent two or more distinct secondary amides in the presence of a Brønsted base and an imide initiator or precursor thereof. A catalytic metathesis reaction takes place in which acyl group exchange occurs between the two or more distinct secondary amides.

The chemical reaction employed in the inventive methods is carried out under aprotic conditions, more preferably polar, aprotic conditions. Exemplary solvents include toluene, dioxane and diglyme, with diglyme a particularly preferred polar, aprotic solvent. The inventive methods are generally carried out at a reaction temperature of about 90° C. to about 120° C.

As can be appreciated from the foregoing, methods according to the invention utilize a Brønsted base such as, for example, a Grignard reagent, alkyl- or aryl-lithium reagent, salt of conjugate base of amine and salt of conjugate base of alcohol. In certain embodiments, the Brønsted base is selected from the group consisting of $NaN(SiMe_3)_2$, $KN(SiMe_3)_3$, KH, MeMgCl, KOtBu and $LiN(SiMe_3)_2$.

The inventors have utilized several exemplary imide initiators including, but not limited to, the acyclic imides N-benzyldiacetamide or N-methyldiacetamide. In certain embodiments, the imide initiator is provided in precursor form which provides, in situ, the respective imide initiator. Suitable precursors include acylating agent such as, for example, acyl halide, acyl imidazole, carboxylic acid anhydride, carboxylic acid ester and mixed anhydride molecules. Particularly preferred precursors include acetyl chloride and acetyl imidazole.

Methods according to the invention display a considerable degree of robustness in terms of amide substrates. For example, two distinct secondary amides reacted in the present methods may be an N-aryl/N-aryl amide reactant pair, an N-aryl/N-alkyl amide reactant pair, or an N-alkyl/N-alkyl amide reactant pair. In the embodiments directed to N-alkyl/N-alkyl amide reactant pairs, those pairs are preferably provided in non-enolizable forms.

The inventors' publication entitled "Catalytic Metathesis of Simple Secondary Amides" (*Agnew. Chem. Int. Ed.* 2007, 46, 761-763) is incorporated herein by reference in its entirety, including supporting information provided on the date of that publication at the website www.angewandte.org.

The following examples describing materials and methodology are offered for illustrative purposes only, and are not intended to limit the scope of the present invention.

EXAMPLES

Example 1

Materials and General Methods

All commercially available compounds were purchased from Aldrich and used as received except N-methyldiacetamide and N-benzoylimidazole (Alfa Aesar). Gas Chromatography was performed with a Shimadzu GC-17A gas chromatograph equipped with a 15 m RTX-5 capillary column (Restek).

The general procedure for amide metathesis reactions was carried out as follows. In a disposable 4-mL vial, a 1:1 mixture of amides (0.23 mmol) and 20 mol % base (0.046 mmol) were mixed in 0.8 mL of diglyme under nitrogen atmosphere in the glove box. To this mixture, 20 mol % imide initiator (0.046 mmol) and triphenylmethane (0.018 mol, 4.4 mg) internal standard was added. The vials were sealed under nitrogen and placed into a 48-well parallel reactor mounted on a Large Capacity Mixer (Glas-Col). The reactions were heated to 120° C. for 18 h and quenched with 1 mL water. The organics were extracted into diethyl ether. Product ratios were determined by GC yields relative to triphenylmethane. The GC method heated at an initial temperature of 135° C. for 2 min followed by 20° C./min ramp to a final temperature of 205° C.

Example 2

Data Related to Product Characterization

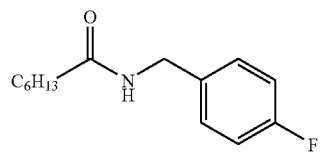

$^1$H NMR (300 MHz, CDCl$_3$) δ: 7.23 (dd, J=5.8, 8.7 Hz, 2H), 6.99 (t, J=8.7 Hz, 2H), 5.85 (s, 1H), 4.38 (d, J=5.8 Hz, 2H), 2.19 (t, J=7.7 Hz, 2H), 1.63 (m, 2H), 1.28 (m, 6H), 0.87 (m, 3H).

$^{13}C\{^1H\}$ NMR (75 MHz, CDCl$_3$) δ: 173.2, 164.0, 160.7, 134.6, 129.7, 115.8, 115.5, 43.0, 37.0, 31.7, 29.2, 25.9, 22.7, 14.2.

HRMS: m/z (ESI) Calculated [MNa]$^+$ 260.1427; measured 260.1439.

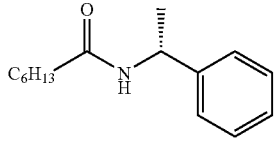

$^1$H NMR (300 MHz, CDCl$_3$) δ: 7.34 (m, 5H), 5.72 (s, 1H), 5.14 (pent, J=7.1 Hz, 1H), 2.16 (t, J=8.1 Hz, 2H), 1.62 (m, 2H), 1.48 (d, J=7.1 Hz, 3H), 1.28 (m, 6H), 0.87 (m, 3H).

$^{13}C\{^1H\}$ NMR (75 MHz, CDCl$_3$) δ: 172.4, 143.5, 128.9, 127.5, 126.3, 48.7, 37.1, 31.7, 29.1, 25.9, 22.7, 21.9, 14.2.

HRMS: m/z (ESI) Calculated [MH]$^+$ 234.1858; measured 234.1847.

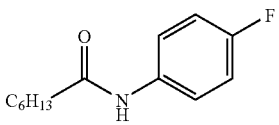

$^1$H NMR (300 MHz, CDCl$_3$) δ: 7.46 (m, 2H), 7.26 (s, 1H), 7.00 (t, J=8.6 Hz, 2H), 2.33 (t, J=7.3 Hz, 2H), 1.71 (m, 2H), 1.32 (m, 6H), 1.28 (m, 6H), 0.87 (m, 3H).

$^{13}C\{^1H\}$ NMR (75 MHz, CDCl$_3$) δ: 172.4, 161.1, 157.9, 134.4, 122.3, 122.2, 115.7, 115.4, 37.7, 31.8, 29.2, 22.7, 14.2.

HRMS: m/z (ESI) Calculated [MH]$^+$ 244.1450; measured 224.1443

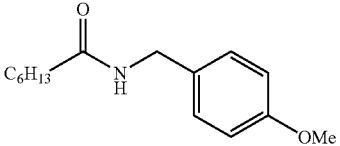

$^1$H NMR (300 MHz, CDCl$_3$) δ: 7.20 (d, J=8.5 Hz, 2H), 6.86 (d, J=8.5 Hz, 2H), 5.65 (s, 1H), 4.36 (d, J=5.6 Hz, 2H), 3.79 (s, 3H), 2.18 (t, J=7.5 Hz, 2H), 1.64 (m, 2H), 1.28 (m, 6H), 0.87 (m, 3H).

$^{13}C\{^1H\}$ NMR (75 MHz, CDCl$_3$) δ: 173.1, 159.2, 130.8, 129.4, 114.3, 55.5, 43.3, 37.1, 31.7, 29.2, 25.9, 22.7, 14.2.

HRMS: m/z (ESI) Calculated [MNa]$^+$ 272.1626; measured 272.1625.

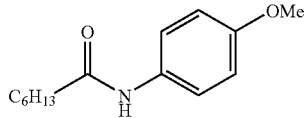

$^1$H NMR (300 MHz, CDCl$_3$) δ: 7.89 (s, 1H), 7.40 (d, J=9.0 Hz, 2H), 6.79 (d, J=9.0 Hz, 2H), 3.75 (s, 3H), 2.29 (m, 2H), 1.67 (m, 2H), 1.27 (m, 6H), 0.87 (m, 3H).

$^{13}C\{^1H\}$ NMR (75 MHz, CDCl$_3$) δ: 172.2, 156.5, 131.6, 128.4, 122.3, 120.1, 114.2, 55.5, 37.6, 31.7, 29.7, 26.0, 22.6, 14.2.

HRMS: m/z (ESI) Calculated [MNa]$^+$ 258.1470; measured 258.1482.

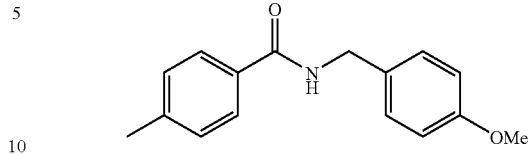

$^1$H NMR (300 MHz, CDCl$_3$) δ: 7.67 (d, J=8.0 Hz, 2H), 7.26 (d, J=8.7 Hz, 2H), 7.21 (d, J=8.0 Hz, 2H), 6.89 (d, J=8.7 Hz, 2H), 6.32 (s, 1H), 4.56 (d, J=5.5 Hz, 2H), 3.80 (s, 3H), 2.38 (s, 3H).

$^{13}C\{^1H\}$ NMR (75 MHz, CDCl$_3$) δ: 167.4, 159.3, 142.1, 131.8, 130.6, 129.5, 127.1, 114.4, 112.3, 55.5, 43.8, 21.6.

HRMS: m/z (ESI) Calculated [MH]$^+$ 278.1157; measured 278.1154.

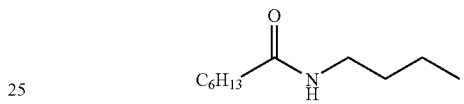

$^1$H NMR (300 MHz, CDCl$_3$) δ: 5.60 (s, 1H), 3.22 (q, J=6.8 Hz, 2H), 2.14 (t, J=7.5, 2H), 1.68-1.18 (m, 11H), 0.94-0.81 (m, 5H).

$^{13}C\{^1H\}$ NMR (75 MHz, CDCl$_3$) δ: 173.3, 39.4, 37.1, 32.0, 31.8, 29.2, 26.0, 22.7, 20.3, 14.2, 13.9.

HRMS: m/z (ESI) Calculated [MH]$^+$ 186.1858; measured 186.1852.

The syntheses and characterizations of the following compounds have been previously reported in the literature: N-phenyl heptanamide: (Lee, S. I.; Son S. U.; Chung Y. K. *Chem. Commun.* 2002, 12, 1310-1311); N-benzyl heptanamide: (Tsuji, Y.; Yoshii, S.; Ohsumi, T.; Kondo, T.; Watanabe, Y. *J. Organometallic Chem.* 1987, 331, 379-385.); N-benzyl acetamide: (Estep, K. G.; Neipp, C. E.; Stephens Stramiello, L. M.; Adam, M. D.; Allen, M. P.; Robinson, S.; Roskamp, E. J. *J. Org. Chem.* 1998, 63, 5300-5301.); N-benzyl-4-methylbenzamide: (Wan, Y.; Alternan, M.; Larhed, M.; Hallberg, A. *J. Org. Chem.* 2002, 67, 6232-6235); N-(4-methoxy-benzyl)-benzamide: (Chesney, A.; Steel, P. G.; Stonehouse, D. F. *J. Comb. Chem.* 2000, 2, 434-437.); N-(4-fluoro-phenyl)-acetamide: (Furuya, Y.; Ishihara, K.; Yamamoto, H. *J. Am. Chem. Soc.* 2005, 127, 11240-11241); N—[(R)-alpha-methylbenzyl]acetamide: (Zeng, Q.-H.; Hu, X.-P.; Duan, Z.-C.; Liang, X.-M.; Zheng, Z. *J. Org. Chem.*, 2006, 71, 393-396.); N,N-diacetylbenzylamine: (Mariella, R. P.; Brown, K. H. *J. Org. Chem.* 1971, 36, 735-737); N-(4-methoxy-benzyl)-acetamide: (Minisci, F.; Punta, C.; Recupero, F.; Fontana, F.; Pedulli, G. F. *J. Org. Chem.*, 2002, 67, 2671-2676.); N-(4-fluoro-benzyl)-acetamide: (Shine, S. J.; Yueh, W. *J. Org. Chem.*, 1994, 59, 3553-3559); N-(4-methylphenyl) heptanamide: (Katritzky, A. R.; Cai, C; Singh, S. K. *J. Org. Chem.* 2006, 71, 3375-3380).

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference.

It is understood that the invention is not confined to the specific reagents, formulations, reaction conditions, etc., herein illustrated and described, but embraces such modified forms thereof as come within the scope of the following claims.

What is claimed is:

1. A method for the catalytic metathesis of secondary amides, comprising the step of reacting in an aprotic solvent two or more distinct secondary amides in the presence of a Brønsted base and an imide initiator or precursor thereof, wherein a catalytic metathesis reaction takes place in which acyl group exchange occurs between said two or more distinct secondary amides.

2. The method according to claim 1, wherein the Brønsted base is selected from the group consisting of Grignard reagent, alkyl- or aryl-lithium reagent, salt of conjugate base of amine and salt of conjugate base of alcohol.

3. The method according to claim 1, wherein the Brønsted base is selected from the group consisting of $NaN(SiMe_3)_2$, $KN(SiMe_3)$, KH, MeMgCl, KOtBu and $LiN(SiMe_3)_2$.

4. The method according to claim 1, wherein the imide initiator is an acyclic imide.

5. The method according to claim 1, wherein the imide initiator is N-benzyldiacetamide or N-methyldiacetamide.

6. The method according to claim 1, wherein said precursor of the imide initiator is an acylating agent, said precursor forming the imide initiator in situ.

7. The method according to claim 6, wherein said acylating agent is selected from the group consisting of acyl halide, acyl imidazole, carboxylic acid anhydride, carboxylic acid ester and mixed anhydride.

8. The method according to claim 6, wherein said acylating agent is acetyl chloride or acetyl imidazole.

9. The method according to claim 1, wherein said reacting step is carried out at a temperature of from about 90° C. to about 120° C.

10. The method according to claim 1, wherein said two distinct secondary amides are an N-aryl/N-aryl amide reactant pair.

11. The method according to claim 1, wherein said two distinct secondary amides are an N-aryl/N-alkyl amide reactant pair.

12. The method according to claim 1, wherein said two distinct secondary amides are an N-alkyl/N-alkyl amide reactant pair.

13. The method according to claim 12, wherein said N-alkyl/N-alkyl amide reactant pair is a pair of non-enolizable amides.

* * * * *